US005354692A

United States Patent [19]
Yang et al.

[11] Patent Number: 5,354,692
[45] Date of Patent: Oct. 11, 1994

[54] ANALYTE DETECTION DEVICE INCLUDING A HYDROPHOBIC BARRIER FOR IMPROVED FLUID FLOW

[75] Inventors: Hsin M. Yang; Michael Newton, both of San Diego; Ping Liu, La Jolla, all of Calif.

[73] Assignee: Pacific Biotech, Inc., San Diego, Calif.

[21] Appl. No.: 941,667

[22] Filed: Sep. 8, 1992

[51] Int. Cl.$^5$ ............... G01N 33/543; G01N 33/558
[52] U.S. Cl. ........................ 436/514; 422/56; 422/57; 422/58; 435/805; 435/970; 436/169; 436/170; 436/518; 436/527; 436/530; 436/531; 436/805; 436/810
[58] Field of Search ................. 422/55–58; 435/805, 970; 436/514, 518, 527, 530, 531, 169, 170, 805, 810

[56] References Cited

U.S. PATENT DOCUMENTS

| | | | |
|---|---|---|---|
| 3,011,874 | 1/1960 | Deutsch | 422/56 |
| 3,211,645 | 10/1965 | Ferrari | 210/22 |
| 3,420,205 | 1/1969 | Morison | 116/114 |
| 3,551,555 | 12/1970 | Schuurs | 424/12 |
| 3,691,017 | 5/1970 | Brown et al. | 195/103.5 R |
| 3,811,840 | 5/1974 | Bauer et al. | 23/253 |
| 3,850,752 | 11/1974 | Schuurs et al. | 424/12 |
| 3,888,629 | 6/1975 | Bagshawe | 422/58 |
| 3,895,914 | 7/1975 | Alberty et al. | 252/408 |
| 3,902,847 | 9/1975 | Busch et al. | 23/230 B |
| 3,915,647 | 10/1975 | Wright | 23/230 B |
| 3,961,899 | 6/1976 | Trivedi et al. | 195/127 |
| 3,966,897 | 6/1976 | Renn et al. | 424/12 |
| 3,979,509 | 9/1976 | Glaever | 424/12 |
| 3,990,849 | 11/1976 | Lee et al. | 356/36 |
| 3,996,006 | 12/1976 | Pagano | 23/253 |
| 4,001,583 | 1/1977 | Barrett | 424/12 |
| 4,017,261 | 4/1977 | Svoboda et al. | 252/408 |
| 4,039,552 | 8/1977 | Adams et al. | 424/12 |
| 4,067,959 | 1/1978 | Bolz | 424/12 |
| 4,092,408 | 5/1978 | Litt | 424/12 |
| 4,094,647 | 6/1978 | Deutsch et al. | 436/810 |
| 4,125,372 | 11/1978 | Kawai et al. | 422/57 |
| 4,138,474 | 2/1979 | Updike | 422/101 |
| 4,168,146 | 9/1979 | Grubb et al. | 422/56 |
| 4,169,138 | 9/1979 | Jonsson | 422/57 |
| 4,180,383 | 12/1979 | Johnson | 422/69 |
| 4,185,084 | 1/1980 | Mochida et al. | 424/12 |
| 4,190,496 | 2/1980 | Rubenstein et al. | 435/7.9 |
| 4,193,983 | 3/1980 | Ullman et al. | 424/12 |

(List continued on next page.)

FOREIGN PATENT DOCUMENTS

| | | |
|---|---|---|
| 0342913 | 11/1989 | European Pat. Off. |
| 0323605 | 12/1989 | European Pat. Off. |
| 0421294 | 4/1991 | European Pat. Off. |
| 9201226 | 1/1992 | PCT Int'l Appl. |
| 9114942 | 3/1991 | World Int. Prop. O. .......... 422/58 |

OTHER PUBLICATIONS

Sears, et al., "Human Immune Response to Monoclonal Antibody Administration Is Dose-Dependent," Arch Surg., vol. 122, pp. 1384–1388, Dec. 1987.

Primary Examiner—Toni R. Scheiner
Assistant Examiner—Christopher L. Chin
Attorney, Agent, or Firm—Knobbe, Martens, Olson & Bear

[57] ABSTRACT

An immunochromatographic assay device for the detection of an analyte in a liquid sample, the device including a housing that contains an opening for the application of the liquid sample and multiple liquid permeable materials located in the housing that are adapted to receive, treat and facilitate the movement of the sample through the housing; preferably, a first liquid permeable material is adapted to receive the liquid sample; a second liquid permeable material is positioned under the first liquid permeable material; a third liquid permeable material is positioned above the second liquid material; means are provided to prevent liquid communication between the first and third liquid permeable materials; a wicking material, in fluid contact with the third liquid permeable material receives the sample; and reagents are positioned in the housing that display the results of the immunoassay.

25 Claims, 4 Drawing Sheets

U.S. PATENT DOCUMENTS

| | | | |
|---|---|---|---|
| 4,205,058 | 5/1980 | Wagner et al. | 422/61 |
| 4,208,479 | 6/1980 | Zuk et al. | 424/12 |
| 4,212,742 | 7/1980 | Solomon et al. | 210/247 |
| 4,225,557 | 9/1980 | Hartl et al. | 422/56 |
| 4,225,784 | 9/1980 | Barrett | 424/12 |
| 4,230,683 | 10/1980 | Decker et al. | 424/12 |
| 4,233,402 | 11/1980 | Maggio et al. | 424/12 |
| 4,235,601 | 11/1980 | Deutsch et al. | 435/4 |
| 4,246,339 | 1/1981 | Cole et al. | 435/287 |
| 4,248,965 | 2/1981 | Mochida et al. | 424/12 |
| 4,256,693 | 3/1981 | Kondo et al. | 422/57 |
| 4,277,560 | 7/1981 | Gray et al. | 422/81 |
| 4,278,653 | 7/1981 | Harris et al. | 422/61 |
| 4,298,687 | 11/1981 | Maes | 424/12 |
| 4,301,249 | 11/1981 | Markus et al. | 435/239 |
| 4,302,536 | 11/1981 | Longenecker | 435/188 |
| 4,305,924 | 12/1981 | Piasio et al. | 422/61 |
| 4,317,810 | 3/1982 | Halbert et al. | 422/61 |
| 4,360,358 | 11/1982 | Sharma | 422/61 |
| 4,361,647 | 11/1982 | Remington et al. | 435/7.94 |
| 4,366,241 | 12/1982 | Tom et al. | 435/5 |
| 4,373,932 | 2/1983 | Gribnau et al. | 436/501 |
| 4,376,110 | 3/1983 | David et al. | 436/548 |
| 4,391,904 | 7/1983 | Liman et al. | 435/805 |
| 4,424,279 | 1/1984 | Bohn et al. | 436/534 |
| 4,425,438 | 1/1984 | Bauman et al. | 436/527 |
| 4,447,529 | 5/1984 | Greenquist et al. | 422/56 |
| 4,461,829 | 7/1984 | Greenquist | 422/56 |
| 4,472,498 | 9/1984 | Masuda et al. | 422/57 |
| 4,533,629 | 8/1985 | Litman et al. | 435/810 |
| 4,552,839 | 11/1985 | Gould et al. | 436/536 |
| 4,582,792 | 4/1986 | Kasahara et al. | 436/523 |
| 4,594,327 | 6/1986 | Zuk | 435/805 |
| 4,595,661 | 6/1986 | Cragle et al. | 436/534 |
| 4,618,475 | 10/1986 | Wang | 422/58 |
| 4,623,461 | 11/1986 | Hossom et al. | 422/101 |
| 4,637,978 | 1/1987 | Dappen | 435/25 |
| 4,649,121 | 3/1987 | Ismail et al. | 436/14 |
| 4,670,381 | 6/1987 | Frickey et al. | 422/56 |
| 4,672,024 | 6/1987 | Giaever et al. | 422/56 |
| 4,690,907 | 9/1987 | Hibino et al. | 436/518 |
| 4,703,017 | 10/1987 | Campbell et al. | 422/55 |
| 4,704,255 | 11/1987 | Jolley | 422/101 |
| 4,727,019 | 2/1988 | Valkirs et al. | 436/531 |
| 4,740,468 | 4/1988 | Weng et al. | 436/501 |
| 4,774,192 | 9/1988 | Terminiello et al. | 436/530 |
| 4,780,280 | 10/1988 | Berger et al. | 422/56 |
| 4,837,168 | 6/1989 | de Jaeger et al. | 436/533 |
| 4,843,000 | 6/1989 | Litman et al. | 435/188 |
| 4,849,338 | 7/1989 | Litman et al. | 436/518 |
| 4,855,240 | 8/1989 | Rosenstein et al. | 436/514 |
| 4,857,453 | 8/1989 | Ullman et al. | 436/514 |
| 4,861,711 | 8/1989 | Friesen et al. | 422/56 |
| 4,912,034 | 3/1990 | Kalra et al. | 422/58 |
| 4,916,056 | 4/1990 | Brown, III et al. | 435/810 |
| 4,943,522 | 7/1990 | Eisinger et al. | 435/810 |
| 4,960,691 | 10/1990 | Gordon et al. | 436/530 |
| 4,962,023 | 10/1990 | Todd et al. | 436/804 |
| 4,981,786 | 1/1991 | Dafforn et al. | 422/56 |
| 4,999,285 | 3/1991 | Stiso | 422/56 |
| 5,073,344 | 12/1991 | Smith et al. | 422/69 |
| 5,120,643 | 6/1992 | Ching et al. | 422/56 |
| 5,202,268 | 4/1993 | Kuhn et al. | 422/58 |

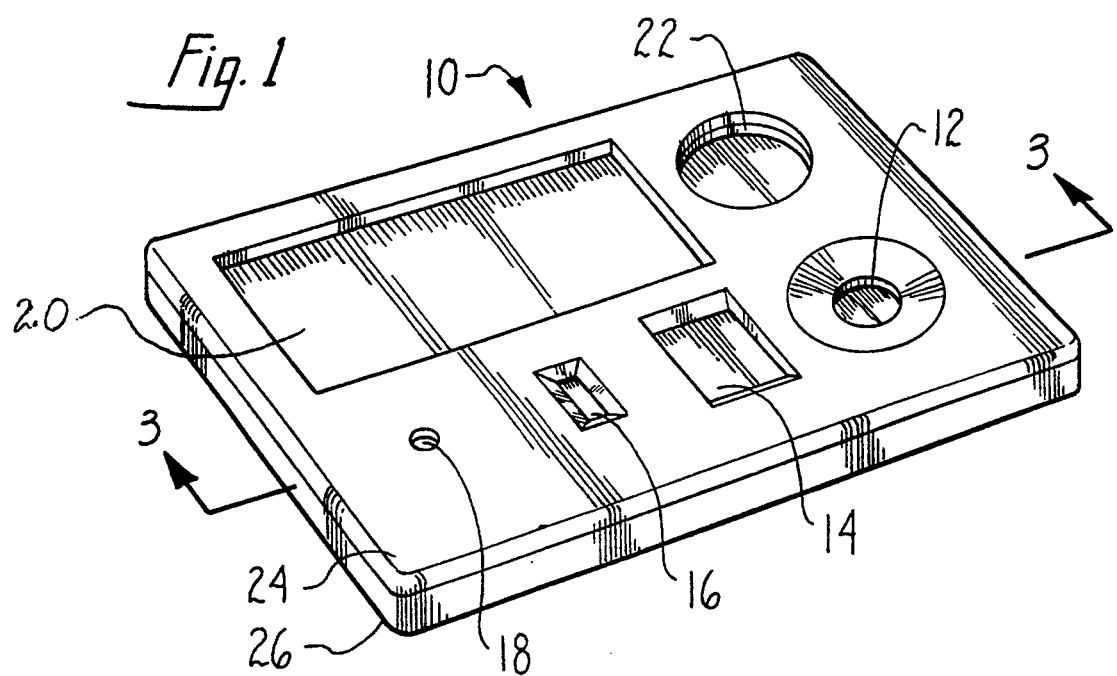
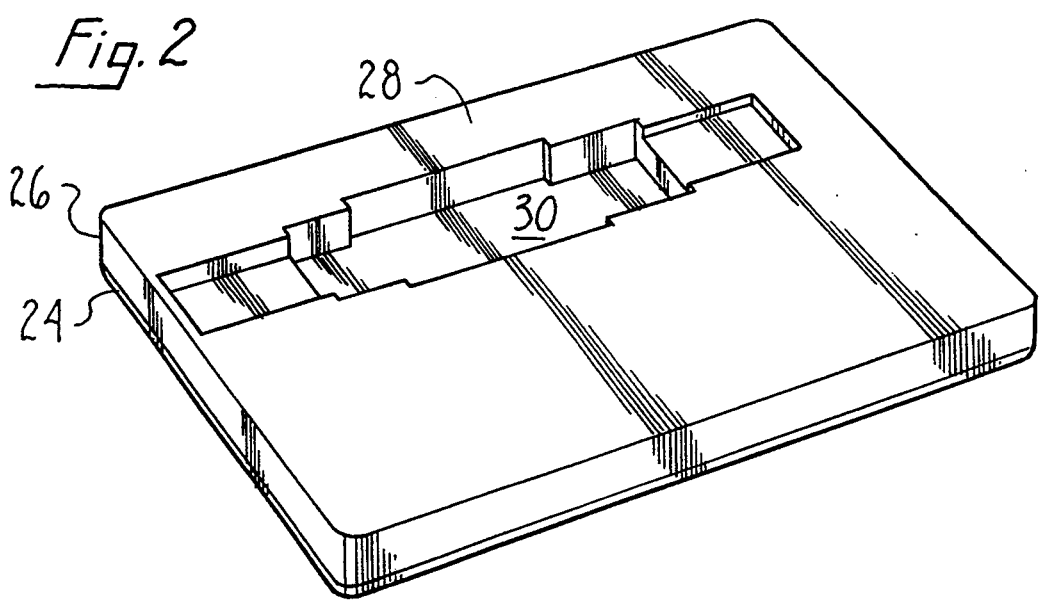

ANALYTE DETECTION DEVICE INCLUDING A HYDROPHOBIC BARRIER FOR IMPROVED FLUID FLOW

FIELD OF THE INVENTION

This invention relates to medical devices suitable for detecting the presence of a particular analyte in a biological sample. More particularly this invention relates to immunochromatographic devices.

BACKGROUND OF THE INVENTION

A number of devices for the detection of a given analyte in a biological sample are available in a variety of design formats. In addition to devices requiring a multiplicity of tubes, vials and support structures, immunoassay devices are encased in housings or casings of varying designs, shapes and colors. One-step assays are those assays in which the user adds a biological sample to a sample application port and receives a positive or negative signal corresponding to the presence or absence of a test analyte in the biological sample. These assays are complex devices that must incorporate into the assay housing a number of immunochromatographic elements. Since the one-step assay has a limited means for sample manipulation, design variations that reduce the number of false positives and improve the sensitivity of the assays are a significant improvement to the art.

There are a number of one-step immunochromatographic assay devices available in the art. These systems all generally permit a sample to be introduced into a receiving port. The sample is placed in contact with a particular reagent which is most often linked to a chromogenic tag. Detectable molecules in the sample complex with reagent and are wicked through the assay where they are ultimately immobilized, usually by a second reagent specific for the test analyte, in a position that generates a positive reaction signal. Additional signals included in the assay provide a negative reaction indicator and test complete indicator.

Immunochromatographic assays of this sort may have a number of potential problems. If the flow of liquid from the sample through the wicking material is too fast, the detectable molecules cannot keep up. They are left behind and are not accurately detected by the assay. The choice of assay materials and their dimensions determine the rate of liquid flow through the assay. The materials and dimensions also influence the evenness of the flow of the detecting molecules through the assay as well as the compatibility of various analytes testable with the sample. Both of these features influence the accuracy of the assay.

In addition, one-step assay results are often compromised by the presence of water marks on the wicking surface that result from liquid pooling beneath the surface. Excess liquid in a one step assay not only creates water marks that may be falsely interpreted as a positive signal, but the excess fluid can flood the one-step device and produce false-negative signals.

SUMMARY OF THE INVENTION

The assay system disclosed herein provides important improvements to the art. For example, this invention provides a more even flow of sample through the apparatus with a shorter assay time, in addition to limiting flooding and the appearance of water marks. The invention additionally provides a wider compatibility with various analytes in the test sample. Further, the configuration of the apparatus provides at least two distinct reaction compartments that are not in direct fluid communication with one another. These separate sample treatment chambers advantageously enable incorporation of a number of successive sample manipulations into a one-step assay.

Specifically, the invention comprises an immunochromatographic assay device for the detection of an analyte in a liquid sample, and a method for using that device. The assay device preferably includes a housing that contains an opening for the application of the liquid sample and multiple liquid permeable materials located in the housing that are adapted to receive, treat and facilitate the movement of the sample through the housing. In a preferred embodiment of the invention, a first liquid permeable material is adapted to receive the liquid sample and a second liquid permeable material is positioned under the first liquid permeable material. A third liquid permeable material is positioned above the second liquid material and means are provided to prevent direct liquid communication between the first and third liquid permeable materials. A wicking material, in fluid contact with the third liquid permeable material receives the sample. Reagents are positioned in the housing that display the results of the immunoassay.

One embodiment of the invention comprises an immunochromatographic assay device, comprising a housing having an opening for introduction of a sample, first liquid permeable material in the housing under the opening adapted to receive a liquid sample introduced through the opening and defining a sample receiving zone, second liquid permeable material in the housing under the first liquid permeable material, adapted to receive sample from the first liquid permeable material, the second liquid permeable material being absorbent and defining a sample transport zone, third liquid permeable material in the housing adjacent the first liquid permeable material, and adapted to receive sample from the second liquid permeable material, the third liquid permeable material located on top of the second liquid permeable material, a hydrophobic material interposed between the first and third liquid permeable materials to prevent direct transfer of sample from the first liquid permeable material to the third liquid permeable material, an elongated sheet of wicking material in fluid contact with the third liquid permeable material adapted to receive sample therefrom, and reagents operably located in the housing to display the results of an immunoassay of the sample. In one embodiment, the first and third liquid permeable materials and the hydrophobic material are physically joined together into an integral sheet, which is separate from the second liquid permeable material. In another embodiment, the first liquid permeable material may be porous thermoplastic polymer. The third liquid permeable material may also be porous thermoplastic polymer. In either case, the porous thermoplastic polymer may advantageously be high density polyethylene. The pore size of the first liquid permeable material is preferably smaller than the pore size of the third liquid permeable material. The first liquid permeable material preferably has a pore size of not greater than about 300 microns and acts to filter the sample introduced into the device.

Another aspect of the present invention relates to an improved immunochromatographic assay device comprising a housing, a sample receiving zone, a liquid permeable material supporting a detecting reagent to detect the presence of an analyte in a fluid sample, an elongate sheet of wicking material, and reagents operably located in the housing to display the results of an immunoassay, wherein the improvement comprises means for preventing direct fluid communication between the sample receiving zone and the liquid permeable material supporting the detecting reagent. In one embodiment of this assay, the sample receiving zone is adapted to pretreat the fluid sample. Furthermore, the fluid sample may be optionally pretreated with immobilized antibody from an animal immunized with a control fluid sample from a human. It is preferred that the control fluid sample tests negative in the immunochromatographic assay.

In the assays of the present invention, the means for preventing direct fluid communication between the first and third liquid permeable materials advantageously comprises a hydrophobic barrier. This barrier may, for example, be polypropylene hot melt adhesive, or other liquid-impermeable thermoplastic polymer.

The invention further comprises a sample treatment pad for use in a immunochromatographic assay comprising at least two liquid permeable materials separated by a hydrophobic barrier but joined by a third liquid permeable material. Preferably, at least one of the liquid permeable materials is a porous thermoplastic polymer. The hydrophobic barrier may advantageously be polypropylene, silicone, rubber, or high density polyethylene.

In yet another preferred embodiment of the disclosed invention, means are provided for preventing flooding in the assay device. Preferably the means for preventing flooding is a divider that controls the flow of liquid from the liquid permeable materials to the wicking material and in a still more preferred embodiment, the means additionally includes a depression positioned adjacent to the divider to collect liquid flooding in the housing.

The present assay system is suitable for use with, but not limited to, both design housings disclosed herein. This assay system could additionally be incorporated in the housing design that is the subject of U.S. Design Pat. No. 324,426. Similarly this design could be incorporated into any number of other housings. The assay design permits the qualitative and/or semiquantitative analysis of biologic reagents using a colored immunochromatographic technique.

BRIEF DESCRIPTION OF THE FIGURES

FIG. 1 is a top perspective view of a preferred housing configuration suitable for accommodating the assay configuration of this invention.

FIG. 2 is a bottom perspective view of the preferred housing configuration of FIG. 1.

DETAILED DESCRIPTION OF THE INVENTION

Figure 5:
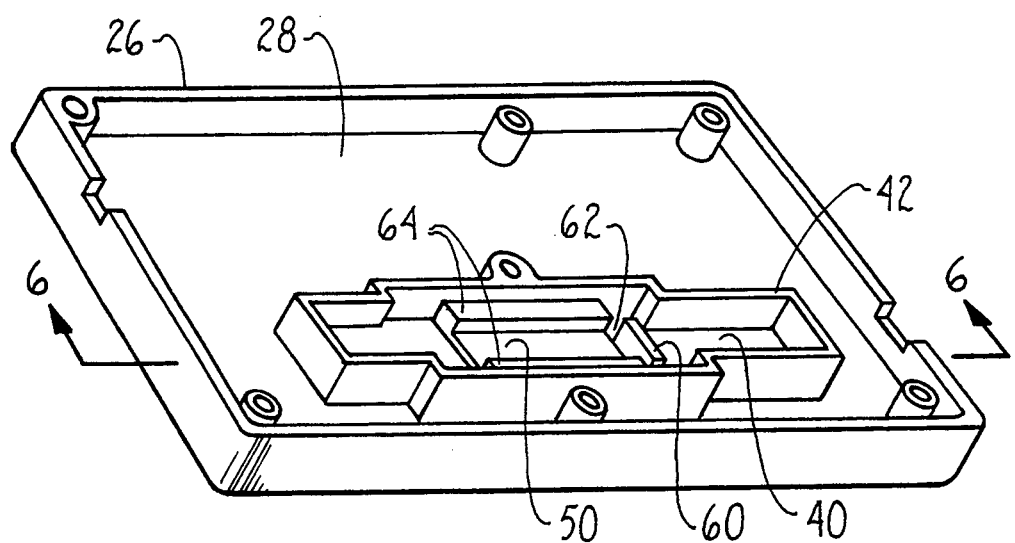
FIG. 5 is a top perspective view of another preferred embodiment of this invention.

In one embodiment of the invention, the assay system is assembled into the housing illustrated in FIG. 1 and in another embodiment of the invention, the assay system is assembled into the housing illustrated in FIG. 5. Corresponding elements of both embodiments are labelled with the same reference numbers. Referring to FIG. 1, the housing device 10 contains a sample application well 12. Samples suitable for application to sample application well 12 include, but are not limited to, body fluids such as urine, blood, serum, extracted materials from swabs or feces, or a combination thereof.

The housing additionally contains a result window 14 positioned between an assay complete window 16 and the sample application well 12. A vent port 18 is optionally included on the upper casing surface. Other apertures located on the top portion of the housing preferably include a desiccant port 20 and a support well 22. In one embodiment, the support well 22 is used to support a sample cup.

FIG. 2 is a bottom perspective view of the same housing configuration as diagrammed in FIG. 1. Preferably the housing is assembled with the immunochromatographic reagents placed in the lower casing 26. Upper casing 24 is sealed over the top. FIG. 2 provides a bottom perspective view of the underside of the assembled housing. The lower casing surface 28 is preferably recessed to provide a multi-tiered support ledge 30 for the wicking material associated with the immunochromatographic assembly discussed in association with FIG. 4.

Figure 4:
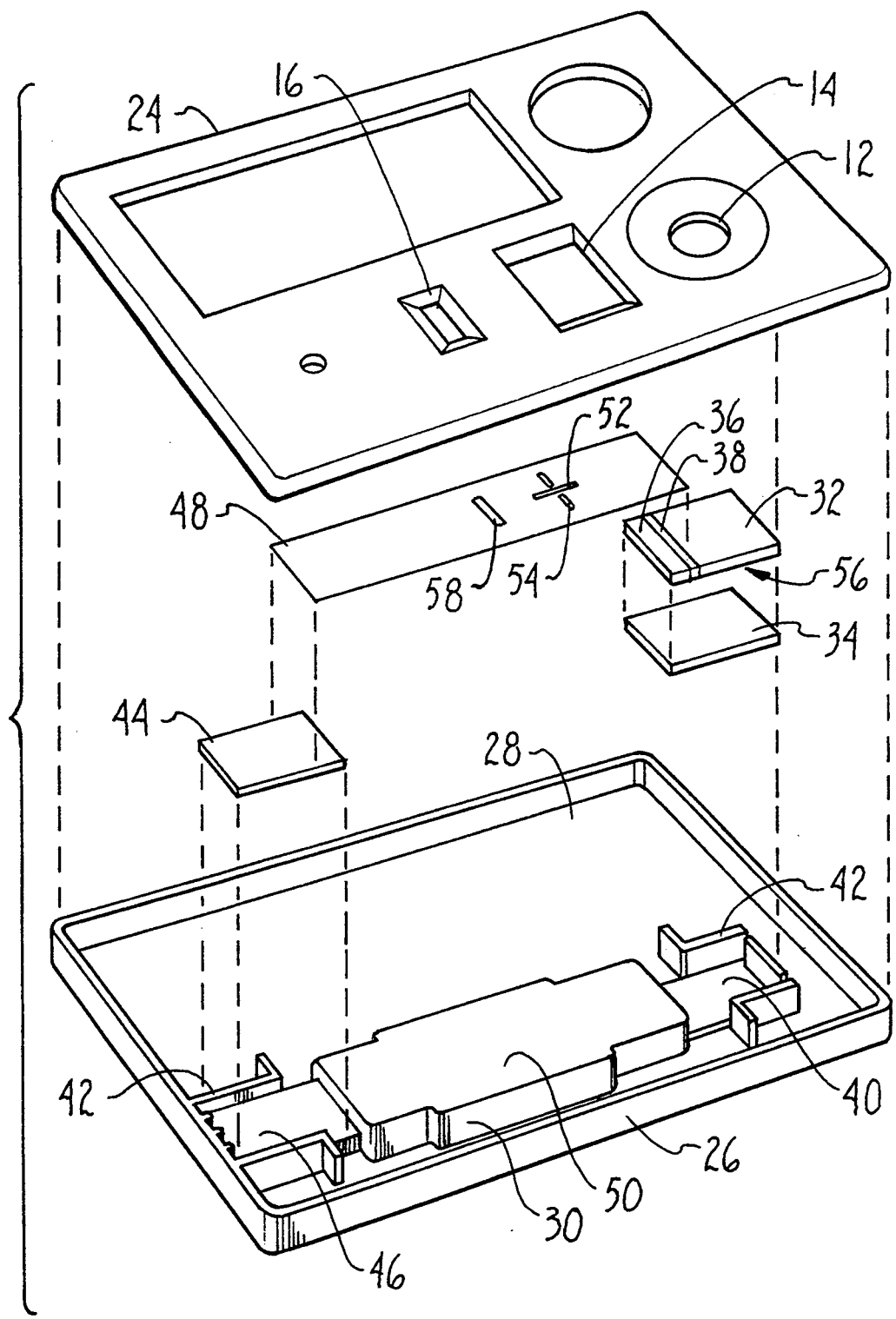
FIG. 4 is an expanded perspective view of the immunochromatographic elements assembled into the housing of FIGS. 1 and 2.

FIG. 4 is an expanded view of the preferred disassembled apparatus complete with the minimum immunochromatographic elements contemplated within the scope of this invention. The chromatographic assembly is positioned along the multi-tiered support ledge 30. In the embodiment of FIG. 4, a first liquid permeable material 32 is assembled on top of a second liquid permeable material 34. In this embodiment, a third liquid permeable material 36 is additionally positioned on top of the second liquid permeable material.

This embodiment also includes a hydrophobic material 38 positioned between the first liquid permeable material 32 and the third liquid permeable material 36. The hydrophobic material 38 prevents fluid communication between liquid permeable materials 32 and 36. In a preferred embodiment of this invention, the first liquid permeable material 32, the hydrophobic material 38 and the third liquid permeable material 36 are assembled together as a single unit, the sample treatment pad 56. Assembly may be facilitated, for example, with adhesive or ultrasonic welding. This unit is positioned on top of the second liquid permeable material 34 and both of these are placed on the first tier 40 of support ledge 30. Support arms 42 are preferably affixed along the lower casing to both position the liquid permeable materials and to support the upper casing. The hydrophobic barrier 38 may comprise any water-impermeable material, such as hot melt adhesive (typically polypropylene), other polymeric or otherwise water-impermeable adhesive, sheets or blocks of plastic material such as polyethylene (including high density polyethylene), PVC, silicone, rubber, and the like.

An absorbent pad is positioned on the second support tier 46 between support arms 42. A wicking material is placed on top of the third support tier 50. The wicking material 48 extends, in length, beyond the third support tier 50 to overlap and contact both the third liquid permeable material 36 and the absorbent pad 44.

The upper casing is positioned on top of the lower casing such that the sample application well 12 is in direct communication with the first liquid permeable material 32. The wicking material 48 extends beneath both the result window 14 and the assay complete window 16. The ventilation port 18 is positioned above the absorbent pad 44. This port optionally aids wicking action by permitting the pad to dry during the assay.

The liquid permeable materials (32, 34 and 36), the absorbent material 44 and the wicking material 48 are supported by the first 40, second 46 and third 50 tiers respectively of the multi-tiered support ledge 30. The support arms 42, illustrated by cross-section, align the permeable and absorbent materials and support upper casing 24.

The immunochromatographic reagents are assembled onto the lower casing 26. The upper casing 24 is affixed to the lower casing 26 using any number of techniques known in the art that include but are not limited to peg and groove snap fit mechanisms, adhesives, snap latches, or the like.

Figure 3:
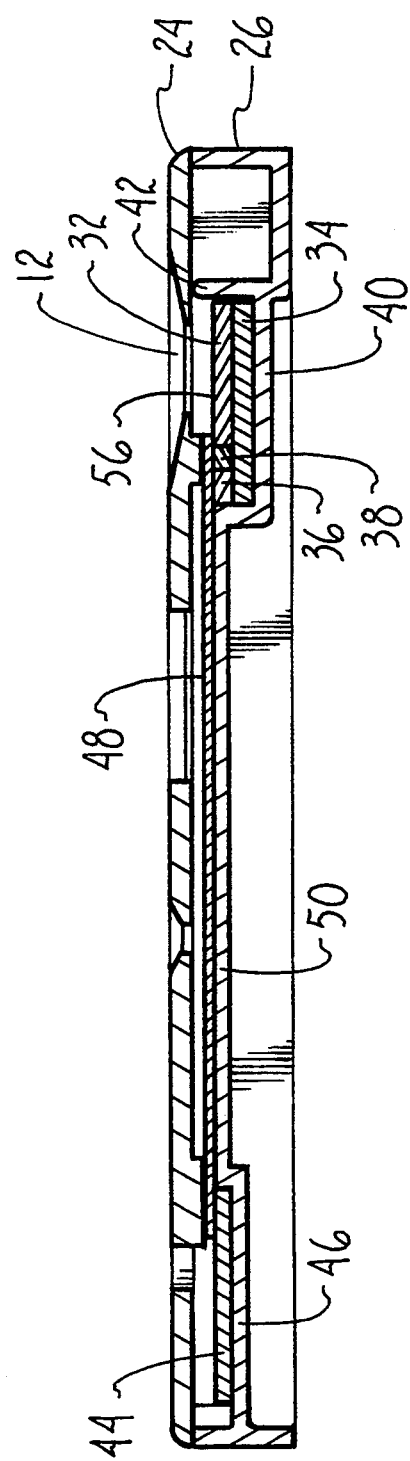
FIG. 3 is a cross-sectional view of a preferred embodiment of the immununochromatographic elements of this invention, positioned in the housing illustrated in FIGS. 1 and 2.

FIG. 3 provides a cross-sectional view through the upper 24 and lower 26 casings of the assembled apparatus of FIG. 4. For purposes of this explanation, the sample application well is at the "top" of the device and sample added thereto goes "down" into the device. When a biological fluid sample of interest is added to the sample application well 12, the fluid passes down through the first liquid permeable material 32 and down into the second liquid permeable material 34. The liquid moves across (to the left in FIG. 3) the second liquid permeable material and up into the third liquid permeable material 36 and onto the wicking material 48. The hydrophobic material 38 positioned between the first and third liquid permeable materials creates a barrier to direct liquid passage therebetween and instead directs fluid flow from the first into the second liquid permeable material.

Fluid travels across the wicking material (to the left in FIG. 3) driven in part by the sample size, sample type, sample viscosity, by the choice of material for the absorbent pad 44, and (of course) by capillary action. Thus, a given volume of urine will likely travel more quickly through a given apparatus than an equivalent volume of serum. The flow is additionally controlled by the choice of liquid permeable materials as well as by the selection and size of the wicking material. Those of skill in the art will appreciate that the pore size of the liquid permeable materials 32, 34, 36 is an important factor in determining flow rate. Furthermore, the pore size of the first liquid permeable material 32 is preferably small enough to filter out and retain unwanted particulates that may be present in the sample, and large enough to allow the fluid to flow at the desired rate. The second liquid permeable material 34 should allow the flow of sample fluid and dissolved pad buffer (previously immobilized in the liquid permeable material), with minimal binding of the analytes to be assayed.

The flow rate of liquid in the sample through the apparatus is important to the sensitivity of the assay. If the liquid moves at a faster rate than the analyte, the wicking action may cease before analyte is detected by the assay. If the liquid moves too slowly, assay time may be slowed and a positive reaction signal may require extended assay times. Assay time is additionally influenced by the overall length between the first liquid permeable material 32 and absorbent pad 44.

In a preferred embodiment of the invention, the first and third liquid permeable materials are prepared from a nonabsorbent, non-reactive porous material such as a high density polyethylene. One example of a high density polyethylene material contemplated for use in this invention is POREX TM (Porex Technologies, Fairburn, Ga.). POREX TM and other similar products are relatively inert and tolerate a variety of different chemicals and pH ranges. POREX TM or other equivalent products are prepared with various pore sizes. POREX TM of various pore sizes can be selected to function as filtration devices, to change sample flow rates or to accommodate different sample sizes. A small pore size filters out particulate from a sample while a medium pore size facilitates flow rates through the apparatus. Therefore, in one embodiment of this invention, the first liquid permeable material is preferably prepared from a small pore high density polyethylene material and the third liquid permeable material is prepared from a medium pore size high density polyethylene material. Suitable size ranges are as follows: small pore size—70 microns$\pm$20 microns; medium pore size—150 microns$\pm$30 microns; large pore size—300 microns$\pm$50 microns.

The second liquid permeable material is preferably an absorbent material, and is exemplified by such commercial products as Whatman Paper No. 1-5, Ahlstrom 939-39 (70% cotton, 30% wood, thickness 0.79 mm), Ahlstrom 9259-R, (thickness 1.12 mm)(Ahlstrom Filtration, Inc., Holly Springs, Pa.), Schleicher & Schuell #930 (100% cotton), or a glass fiber pad such as Gelman Ultrathick Glass Fiber, #66078 (Gelman Co., Ann Arbor, Mich.). Glass fiber pads are useful in whole blood assays to retain blood cells in the pad and allow the serum or plasma sample to flow through. Material used for the second liquid permeable material should be absorbent enough to accept fluid from the first liquid permeable material 32 but not so absorbent that liquid pooled within the second liquid permeable material instead of moving into the third liquid permeable material and onto the wicking material. Other absorbent materials contemplated for use as a second liquid permeable material include but are not limited to polyester materials, such as nonwoven polyester fiber pads or sheets. Absorbent materials may be combined to include a cheesecloth like material combined with a Whatman absorbent pad. The second liquid permeable material could additionally be prepared from any suitable cotton and wood fibrous pad such as the 70% cotton, 30% wood pad material produced by Ahlstrom as #939-39. The second liquid permeable material defines a sample transport zone.

It is contemplated that the first, second and third liquid permeable materials will act in concert to facilitate movement of a sample at an appropriate rate through the third liquid permeable material and onto the wicking material. Most immunochromatographic assays have a completion time ranging from between 1 to 15 minutes. More preferable assay times for one-step assays are between 1-5 minutes. The rate is, in part, determined by the thickness of each of the liquid permeable materials, the viscosity of the sample and the porosity of the liquid permeable materials. The methods for testing and optimizing various combinations of materials, as required for each individual analyte, are well known to those with skill in the art. An assembly with exemplary materials and dimensions is provided in Example 3.

The wicking material is preferably a suitable chromatographic material such as nitrocellulose, nylon, for example BIODYNE ™ (ICN Biochemicals, Inc., Irvine, Calif.) or the like. In a preferred embodiment, the wicking material is prepared from nitrocellulose with a pore size in the range of between 1 to 30 microns. In another embodiment the wicking material is a type of high density polyethylene and in another embodiment the wicking material is provided with a laminated or nonlaminated solid support such as a polyethylene or cellulose. These materials provide stability to the wicking material and can be used to channel the liquid sample along the wicking material. The type of solid support and the choice of porosity of the wicking material will influence flow rate. The wicking material should be suitable for the immobilization of a capture molecule such as an antigen or antibody and for the incorporation of a suitable marker dye. In addition the wicking material may be combined with additional support materials such as cellulose or polyethylene. One with skill in the art of assay design will recognize that the addition of support material to the wicking material will influence both the stream and rate of liquid flow.

Absorbent pad 44 can be prepared from a variety of absorbent materials. The pad is preferably absorbent enough to drive the capillary action of the liquid across the pad. Absorbent materials are well known in the art. Suitable materials include cotton, cellulosic materials, glass fiber, and the like. In one embodiment the absorbent pad is prepared from the same material as the second liquid permeable pad and in another embodiment the absorbent pad is more absorbent than the second liquid permeable material. The absorbent pad is preferably thicker than the second liquid permeable pad and in yet another preferred embodiment the pad is prepared from an absorbent material containing 70% cotton and 30% wood.

The assay configuration of this invention is particularly suited for an immunochromatographic assay to determine the presence or absence of a particular test analyte in a biological sample. The assay configuration can be adapted to detect any number of analytes such as antigen or antibody in a fluid sample. As disclosed above, the assay is particularly suited for biological samples including urine or serum. It is also contemplated that viscous samples such as mucous or saliva could be appropriately diluted or digested with suitable enzymes to decrease the viscosity and applied to this assay system. In addition, biological solids such as feces or solubilized cell preparations could similarly be analyzed using this assay after suspension in an appropriate buffer or treated with nucleases, or the like, to reduce sample viscosity.

To detect a particular analyte in a sample, a suitable antigen or antibody specific for the analyte is labelled with a chromogenic particulate such as latex, selenium, colloidal gold or the like. The term "detecting reagent" is used herein to denote particular antibody or antigen preparations reacting specifically with the analyte. In a preferred embodiment of this invention, the chromogenic particulate is latex. Example 1, below, discloses a useful procedure for the conjugation of latex to the detecting reagent. Latex (MagSphere, Pasadena, Calif.) is available from the manufacturer with a number of reactive groups added to the latex particle. These reactive groups can be used to facilitate conjugation to the detecting reagent. For example, the latex can be carboxylated or amidated. Those with skill in the art will be able to select an appropriate reactive group suitable for conjugation with a detecting reagent of interest.

Further, latex is available in a number of different colors. Color will influence both the assay aesthetics as well as the sensitivity of the assay. For example, a light-colored conjugate may be more difficult to detect than a darker colored conjugate and may therefore render the assay less sensitive. In a preferred embodiment disclosed in the Examples below, darker colored latex particulate is conjugated to an antibody or antigen specific for the analyte. In a particularly preferred embodiment, blue latex particulate is conjugated to antibody. In a specific example outlined in Example 1, 0.433 $\mu$m latex is conjugated to antibody specific for human chorionic gonadotropin (HCG).

The chromogenic particulate conjugated to antibody is preferably applied to the third liquid permeable material. The quantity of particulate conjugated antibody added to the liquid permeable material should be carefully controlled to optimize the sensitivity of the assay and minimize the incidence of false positives.

There are a variety of methods known in the art for applying the latex to a liquid permeable material. As a universal method of application, irrespective of the composition of the liquid permeable material, the liquid permeable material can be encased with a fibrous or woven material soaked in a liquid solution of the conjugated chromogen. Similarly the liquid permeable material can also be dipped into a liquid suspension of the conjugated chromogen. The latex particles must be able to move with the flow of liquid out of the permeable material. Thus, in a preferred embodiment of this invention, the third liquid permeable material is a high density polyethylene and in a particularly preferred the POREX ™ pore size is preferably in the range of 0.1–1.0 micron.

In a preferred method, the conjugated latex is sprayed by air brush onto a high density polyethylene such as POREX ™. Spraying advantageously provides a more even distribution of the chromogen in the liquid permeable material. Methods for finely applying materials by air brush are well known in the art. An exemplary method for applying the chromogen to the liquid permeable material is provided in Example 2.

FIG. 4 provides a preferred conformation for the first and third liquid permeable materials. Here, the first liquid permeable material 32 is affixed to the third liquid permeable material using a hydrophobic material such as an impermeable heat glue, a thermoplastic polymer or the like. One example of a thermoplastic polymer contemplated for use in this invention is a high density polyethylene. This material could be glued or affixed to the first and third liquid permeable materials. The combination of the first liquid permeable material 32, affixed to the third liquid permeable material 36 and separated by a hydrophobic barrier 38 defines the sample treatment pad 56 illustrated in FIG. 4. This pad may be preassembled as a discrete unit. These units can be produced in quantity and each sample treatment pad 56 can be customized to include any number or combination of detecting reagents for any number of assays suitable for the immunochromatographic testing of an analyte in a biological sample. The conjugated latex can be applied to the liquid permeable material before or after the first and third liquid permeable materials are bound together with the hydrophobic material.

Referring to FIG. 3, it is additionally contemplated that any suitable hydrophobic barrier could be positioned between the first and third liquid permeable materials to prevent flow therebetween. For example, in another embodiment of this invention (not shown in the Figures), the upper casing 24 can be prepared with an arm extending from the upper casing to the second permeable material 34 to restrict fluid communication between the first and third liquid permeable materials.

The conformation of the liquid permeable materials provides important advantages to the art of immunochromatographic assays. First, the separation of a first liquid permeable material from direct communication with the liquid permeable material containing the detecting reagent is an important improvement to the art. Second, the separation of these liquid permeable materials in space provides greater control in fluid flow through the device. Therefore, the device is better able to accommodate a number of different rates of sample application. Similarly, the apparatus is better able to accommodate a wider range of sample volumes.

It is contemplated within the scope of this invention that three or more liquid permeable materials could be arranged in fluid communication with one another to direct and process a liquid biological sample. Thus, a more complex device would incorporate multiple liquid permeable materials, some of these preferably containing at least one sample treatment. The liquid permeable materials could add different reagents to the sample, enzymatically treat the sample, provide additional filtration functions or additionally function to reduce the incidence of false positives in the immunochromatographic assay.

An additional advantage of the three-dimensional association of the liquid permeable materials, together with modifications in the choice of materials and the dimensions of the materials in relation to the sample size, is that the conformation provides a means to control the rate of fluid flow from the first liquid permeable material through the second and to the third liquid permeable material. Thus, the first liquid permeable material can be adapted to serve as a sample pretreatment area. In addition the first liquid permeable material functions as sample receiving zone. Sample pretreatment provides a number of important advantages to immunochromatographic assays that are heretofore undisclosed.

For example, a biological sample invariably contains particulate that can prevent even fluid flow through the device. Many samples can be centrifuged to remove gross particulate. However, high-speed centrifugation may be required to remove fine particulate that can significantly alter fluid flow and therefore alter the sensitivity of the assay. In a preferred embodiment of this invention, the first liquid permeable material has a small enough pore size (e.g., 50 to 90 microns) to trap particulate that could influence the accuracy of the immunochromatographic assay.

As another pretreatment regime, the first liquid permeable material can be used to improve the specificity of the assay. For example, antibody or F'(ab)$_2$ fragments reactive with a control sample can be immobilized on the first liquid permeable material. For example, polyclonal antibody, from an animal immunized with a negative control specimen, can be conjugated to latex and immobilized in the first liquid permeable material. Nonspecific molecules in the biological sample would be adsorbed from the sample as it moves through the permeable material. This sample purification step helps to reduce non-specific binding of sample to the detecting reagent.

As an exemplary application of a pretreatment embodiment, an assay is developed for the diagnosis of carcinoembryonic antigen in sera (CEA). Sera from CEA negative donors is injected into rabbits to produce a polyclonal antibody preparation reactive with human sera. Immunoglobulin G is purified from high-titered rabbits using methods well known in the art of immunology. This immunoglobulin is complexed to white latex and immobilized within the first permeable material. The assay is assembled as disclosed supra. A serum sample from a patient containing CEA is applied to the sample application well. As the sample passes through the first liquid permeable material, it contacts immobilized rabbit anti-human immunoglobulin antibody. Common antigens present in the serum are recognized by the rabbit anti-human immunoglobulin. These antigens are immobilized within the first liquid permeable material and reduce the non-specific binding of the CEA specific antigen present in the third liquid permeable material.

It is additionally contemplated that other molecules or compounds could be added to the first liquid permeable material to pretreat the biological sample. Thus, enzymes could be added to digest specific components in the biological sample, to decrease viscosity or improve assay sensitivity. Buffers could be added to alter pH or chemical additives could be incorporated into the first liquid permeable material.

Analyte present in the biological sample passes through the first permeable material, or the sample receiving zone, and into the second permeable material. The second permeable material is assembled onto the device presoaked in a latex mobilizing buffer and then dried. The sample passes through the second permeable material, or sample transport zone, and reconstitutes the dried buffer. The latex mobilizing buffer preferably contains a detergent together with other compounds to help mobilize the latex-bound detecting reagent present in the third permeable material. The buffer may additionally contain casein and sucrose. The buffer may advantageously have a pH of preferably in the range of about 7–9 and more preferably, about 8.0. The buffer preferably contains a buffering agent such as a 5–50 mM solution of Tris(hydroxymethyl)aminomethane (TRIZMA, Sigma, St. Louis, Mo.) or 2-Amino-2-(hydroxymethyl)-1,3-propanediol (TRIS), and more preferably a 20 mM TRIS buffer. The buffer preferably additionally contains 5%–30% sucrose and more preferably about 20% sucrose together with 0.05%–5% zwittergent 3-12 and more preferably about 0.5% zwittergent 3-12 with 0.01%–5% casein and preferably about 0.1% casein. Such a buffer can effectively promote release of latex from the porous material and may additionally be used as a printing solution buffer. An example of a suitable buffer to mobilize detecting reagent (conjugated latex) is provided in Example 3.

The pretreated and buffered sample moves into the third liquid permeable material where it contacts the latex-bound detecting reagent. The latex is mobilized in the buffered sample and follows the liquid front onto the wicking material. Analyte present in the sample binds to the latex bound detecting reagent and the complex passes with the liquid onto the wicking material.

Immobilization of reagents onto the wicking material permits detection of the analyte in the sample. The wicking material 48 is uniquely modified to detect a particular analyte. Returning to FIG. 4, the wicking material 48 is assembled onto the third support tier after a visible horizontal or transverse bar 52 is applied to the wicking material in that area of the wicking material corresponding to the result window 14. The horizontal bar can be applied to the wicking material in any number of methods using any number of compounds recognized to be suitable to the art. As a preferred method, the horizontal bar 52 is airbrushed onto the wicking material 48 using an unconjugated chromogenic particulate identical to the chromogenic particulate conjugated to the detecting reagent. More preferably, the chromogenic particulate is a 0.43 micron latex particulate and the wicking material is 8 micron nitrocellulose. The latex is applied by airbrush to the wicking material in a buffer void of zwitterionic detergents (ZWITTERGENT TM. Calbiochem, San Diego, Calif.) and is allowed to dry. ZWITTERGENT TM help to mobilize the latex particles. Therefore, while ZITTERGENTS TM are included in the dried buffer incorporated into the second liquid permeable material, they are absent to immobilize latex. Exemplary ZWITTERGENTS TM contemplated for use in this invention include but are not limited to ZWITTERGENTS TM 3-8, 3-10, 3-12, 3-14, and 3-16. Other types of detergent or surfactant can also be used, such as ionic and nonionic surfactants.

A vertical bar, parallel to the direction of fluid flow, is additionally applied to the wicking material. The vertical bar 54 is preferably positioned at a 90° angle to the horizontal bar 52 and is preferably centered along this horizontal bar 52. The vertical bar comprises an antibody or other protein capable of binding to the test analyte. The protein is immobilized onto the wicking material due to the hydrophobic interactions between the protein and the wicking material surface. This immobilized protein is preferably different from the detecting reagent and, like the detecting reagent, specifically recognizes the test analyte. It will be recognized by those with skill in the art that the detecting reagent conjugated to latex should not substantially interfere with the binding of the analyte to the protein positioned along the vertical bar 54. Therefore in a preferred embodiment, the detecting reagent and the protein deposited as a vertical bar recognize different epitopes on the analyte. Methods for testing interference between the binding of the detecting reagent and the binding of the protein to be deposited along the vertical bar are well known in the art and include but are not limited to enzyme-linked immunoabsorbent assays, radioimmunoassays, western blots or the like. The vertical bar, like the horizontal bar, is also preferably applied to the wicking material by air brush. This vertical bar is preferably colorless such that visual inspection of the device before sample application reveals only the horizontal bar and this horizontal bar is interpreted as a negative test result.

The chromogenic particulate conjugated to the detecting reagent complexes with analyte in the biological sample as the sample passes from the third permeable material onto the wicking material. As this complex passes across the vertical bar the protein immobilized thereto binds the analyte and concentrates the chromogenic particulate along the vertical bar. Chromogenic particulate not bound to analyte travels past the vertical bar toward the absorbent pad 44. The presence of analyte in the biological sample is detected by visualizing the vertical bar. This invention enhances the visualization of the vertical bar because of the unique configuration of the first, second and third liquid permeable materials and the advantageous benefits associated with the sample pretreatment steps associated, in this embodiment, with the first liquid permeable material.

In the embodiment illustrated in FIG. 4, visualization of the vertical bar together with the horizontal bar produces a cross-hatch or "plus" symbol on the surface of the wicking material that is visible through the result window 14. However, it will be understood by those with skill in the art that there are any number of conformations of the vertical and horizontal bars that could similarly be interpreted to mean the presence or absence of a testing analyte.

In addition, the assay preferably includes an assay complete indicator that is visible through the assay complete window 16. In one embodiment of this invention, chromogenic particulate is conjugated to antibody generated against a common antigen and this conjugate is also applied to the liquid permeable material. Another protein, such as a second antibody, that recognizes the complex of common antigen to chromogen-complexed antibody is applied to the wicking material as a test complete indicator 58 in a position corresponding to the assay complete window 16. The second antibody immobilized onto the wicking material is preferably colorless.

For example, albumin is a common protein present in sera. Albumin present in the biological sample contacts albumin-specific antibody conjugated to blue latex as it passes through the third liquid permeable material. This complex moves across the wicking material, past the vertical and horizontal bars to contact a second albumin-specific antibody positioned on the wicking material in a location corresponding to the assay complete window 16. The second antibody binds the albumin-blue latex complexes. The assay is complete when the area beneath the assay complete window 16 turns blue.

In another example, employed in Example 2, BSA is conjugated to latex and incorporated into the third liquid permeable material together with the complexed analyte-conjugated detecting reagent. Conjugated BSA moves across the wicking material and contacts antibody to BSA immobilized along the test complete bar 58. In addition to providing an indicator for a complete test and a procedural control for the assay, the addition of BSA-latex to the latex printing solution improves the latex flow characteristics.

In another example, a mobile dye such as bromophenol blue or xylene cyanol, Texas red, food dye, or other indicator is applied to the wicking material or to the liquid permeable membrane in a position that is preferably not visible to the user prior to the addition of a test sample. The presence of the dye in the assay complete window or in another window positioned above absorbent pad 44 can be used as an indication of a completed test.

Additionally, it is recognized that false positives can be generated in one-step immunochromatographic assays if the biological sample is obtained from individuals sensitized to mouse, rabbit, goat protein or the like. This antibody can mimic a positive signal by binding the animal specific antibody. Therefore, a third window can be added to this assay to detect nonspecific binding. The detection of nonspecific binding invalidates the assay. For example, if murine antibody is used in the assay then anti-mouse antibody conjugated to latex can be applied in the third liquid permeable material. Other anti-mouse antibody immobilized onto the wicking material can be used to capture the murine antibody complex. Anti-mouse antibody present in the patient sample will bind the latex conjugate and be captured onto the wicking material. A blue signal in this window would indicate an invalid assay. These individuals can be tested by other assays known in the art.

Figure 6:
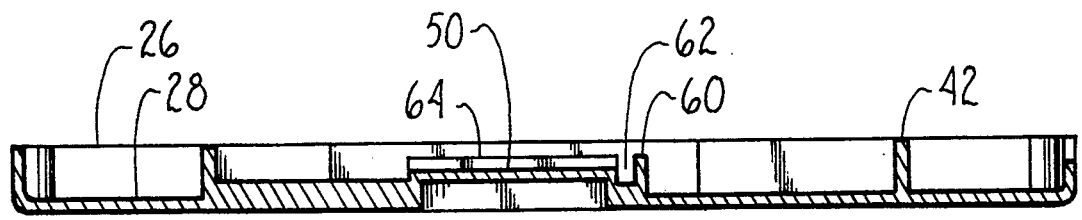
FIG. 6 is cross-sectional view of the embodiment illustrated in FIG. 5 containing the preferred immunochromatographic elements of this invention.

In another preferred embodiment of this invention, provided in FIG. 5, the lower casing 26 is formed to accommodate the assay configuration detailed in FIG. 6. In this embodiment, the first tier 40 is surrounded by the support arms 42 to assist in the positioning of the second liquid permeable material 34 and the sample treatment pad 56. Unlike the embodiment of FIG. 3, a divider 60 is positioned between the sample treatment pad 56 and the third support tier 50. In a preferred embodiment, this divider 60 is a wall that is molded or affixed to the lower casing surface. In addition a depression 62 is formed between the divider 60 and the third support tier 50. In this embodiment, the third support tier 50 is modified to include support rails 64. The support rails are preferably raised surfaces positioned lengthwise, in the direction of fluid flow, along the surface of the second support tier 50. A recess is formed between the ribs along the surface of support tier 50 and this recess provides an additional site for liquid to pool. In a preferred embodiment associated with the dimensions provided in Example 3, the support rails 64 are raised 0.036" above the third support tier surface and the depression 62 is positioned at a height less than the support tier surface. In this embodiment, the height of the support rails 64 from the lower casing surface 28 is equal to the height of the divider 60 from the lower casing surface 28. Therefore, in this embodiment, the wicking material 48 contacts the third liquid permeable material 36, the divider 62, the support rails 64 and the absorbant pad 44. In addition, in this embodiment, the wicking material length is shortened to less than 3.7 cm. to provide a shortened assay time of less than one minute.

The embodiment of FIGS. 5 and 6 has a number of significant advantages for one-step assays. For example, sample pooling and sample flooding within the housing is a problem that can negatively influence assay results. An uncontrolled influx of sample fluid or an excess of fluid on the third support tier that cannot be accommodated by the wicking material, results in the fluid moving by capillary action beneath the wicking material 48. If this fluid moves faster than the liquid front flowing through the wicking material, and the absorbant pad 44 becomes saturated before the assay is complete, the results of the assay are compromised. The divider 60 and depression 62 combine to control fluid flow and accommodate excess fluid in the housing. Moreover, the support rails 64 are provided as support for the wicking material 48. It is contemplated that when the wicking material 48 is positioned onto the third support tier 50, the wicking material preferably only contacts the support rails 64 along the fluid support tier surface. These support rails preferably do not contact the diagnostic surfaces of the wicking material, including the horizontal 52 and vertical 54 bars positioned beneath the result window.

Reduced contact between the third support tier and the wicking material offers important advantages to one-step devices such as those described here. First, like the divider 60 and depression 62, the support rails 64 prevent flooding of sample fluid onto the wicking material. Excess fluid passes along the third support tier 50 surface beneath the support rails 64 and onto the absorbent pad. In addition, reduced contact between the wicking material and the third support tier significantly reduces the incidence of water marks on the wicking surface. Water marks are caused by the retention of fluid accumulating beneath the wicking material and it is possible that the water marks formed from excess fluid trapped beneath the wicking material could be interpreted as a false positive result in other assay configurations.

It is contemplated that there are a variety of variables disclosed both in the discussion above and in the exemplary work detailed below. Those with skill in the art will appreciate that each analyte/detection reagent combination as well as the methods for diagnosing analytes in different biological specimens using different analyte/detection reagent combinations will require individualized testing and optimization. However the methods for altering the assay of this invention to accommodate variations in samples or variations associated with a particular analyte can be readily assessed by someone with skill in the art.

EXAMPLE 1

Latex Conjugation of Reagents

Protocol for Conjugation of Antibody or Antibody Fragment f(ab')$_2$ to Uniform Latex Particles Two-Step Conjugation Procedure: The antibody directed against the analyte of interest may be either polyclonal or monoclonal. Examples used in this assay were mouse anti β-HCG monoclonal antibody, or goat anti-human IgM polyclonal antibody. The antibody can be modified prior to conjugation by digestion with pepsin to yield the f(ab')$_2$ fragments from either monoclonal antibody or polyclonal antibody. Carboxylated uniform latex particles (0.2 to 0.5 microns; from Magsphere Inc. or Seradyn (Indianapolis, Ind.) at a concentration of 0.5% (wt/vol) were activated in the presence of 0.2% EDAC (1-ethyl-3-(3-dimethylaminopropyl)carbodimide) and 0.1% sulfo-NHS (N-hydroxysulfosuccinimide) in 20 mM MES buffer, pH 5.5, for 2 hours at room temperature. The excess amount of EDAC was removed by washing in an Amicon stirrer. Subsequently, an appropriate amount of antibody was added to the latex suspension (here, a weight ratio of 1 mg anti β-HCG antibody to 35 mg latex parties). The mixture was incubated in MES buffer, pH 6.5, at room temperature for 2 hr. At the end of incubation, the solution was sonicated with a probe sonicator to disrupt the microaggregates. The conjugated latex was resuspended to a 3% (wt/vol) concentration in printing solution containing appropriate agents which facilitate lateral latex flow on a porous membrane, such as 20% sucrose, 0.5% casein, 0.5% Zwittergent TM 3-12, and 20 mM Tris-Hcl, pH 8.5. A competitive radioimmunoassay was performed to determine the amount of antibody on each latex particle. A useful concentration of antibody to latex is preferably in the range of 5–100 μg of antibody/mg latex particle and more preferably 10–50 μg and in this particular example, an average of 26 μg antibody/mg of latex particles was used. The concentration of latex particles in a 1:1000 dilution in 0.1% Tween was determined by the absorbance at 500 nm multiplied a constant of 8.65. (This constant is derived from an empirical formulation that will determine the dry weight of 0.433 micron latex particles in solution accurately at 1:1000 dilution with 0.1% TWEEN 20). The antibody-latex is stored at 4° C. until use.

One-step conjugation procedure: The one-step conjugation procedure was also used for conjugating protein to latex. Here the latex particles, antibody of interest, bovine serum albumin and carbodimide were mixed together during the conjugation reaction. This procedure promoted protein-protein conjugation simultaneously with protein-latex conjugation, and produced better results for some protein.

Conjugation of latex to other analytes: Uniform latex particles may be conjugated to other analytes of interest, such as purified or partially purified extracts prepared from micro-organisms or viruses. As one example, a purified extract from *Borrelia burgdorferi* was conjugated to latex particles for the detection of specific anti-Borrelia antibodies in a biological specimen using the conjugation procedures outlined in this example.

Conjugation of latex with Bovine Serum Albumin (BSA) control: To ensure the assay was performed correctly and to determine when the assay is complete, a procedural control was included. Latex conjugated to BSA (BSA-latex) was added to the latex printing solution applied to the third liquid permeable material. For example, the latex printing solution for a serum/urine HCG assay preferably contains 0.6% BSA-latex and 0.8% anti β-HCG latex. BSA-latex was prepared by conjugating BSA to latex particles at a 1:20 ratio (wt/wt) in the presence of EDAC. The conjugated BSA-latex was resuspended to 3% in the printing solution and stored at 4° C. until use.

Sample Pretreatment: Protein was conjugated to latex and immobilized on the first liquid permeable material. White latex was conjugated to a MAK 33 antibody (Boeringer Mannheim Biochemicals, Indianapolis, Ind.) to reduce false positives. (MAK 33 is directed against creatine kinase; however, it has been found that addition of an excess of mouse antibody can eliminate the interference caused by human anti-mouse antibody which may be present in the sample in many immunoassay systems. See Sears, H. F., Arch. Surg. 122:1389 (July-Sept. 1991).)

The conjugate was prepared using the two-step reaction described above. The latex was applied to the liquid permeable material in 20 mM Tris-HCl, pH 8.5 without other latex printing solution ingredients to facilitate the immobilization of latex in the POREX TM piece.

EXAMPLE 2

Application of Latex Conjugated Reagents to the Liquid Permeable Material

The latex printing solution was applied to the hydrophilic, porous polyethylene material (x-4899, Porex Technologies, Atlanta, Ga.). The latex printing solution (provided in Example 1) was deposited into the third liquid permeable material as a spray using an air brush (Iwata, model HP-BC2). The POREX TM was cut into 10 mm×15 mm strips with a paper cutter. The cut POREX TM pieces were then air dried in the presence of desiccant until the pieces were assembled onto the reaction device.

Seventy μl of white MAK33-latex was manually applied onto POREX TM having a pore size of 50–70 microns (used for the first liquid permeable material) and allowed to dry at room temperature in the presence of desiccant.

EXAMPLE 3

Assembly of Exemplary Diagnostic Assay for Human Chorionic Gonadotropin (HCG) in Serum Prior to assembly of the housing device with the assay elements, the liquid permeable materials were treated with the buffers, reagents and the like. The second liquid permeable material, prepared from a cotton filter (Ahlstrom 9259-R), was treated with pad buffer containing 1% Tween, 1% Zwittergent TM 3-12, 1% bovine gamma globulin, 800 μg/ml of rat gamma globulin, 1% rabbit gamma globulin, 1% casein, 10 ug/ml of anti-LH antibody (to eliminate trace amounts of luteinizing hormone present in human urine), and 20 ug/ml of MAK 33 in 200 mM Tris-HCl, pH 8.5. The pads were allowed to soak in the buffer and the filters were dried at 50° C. for 1 hour and stored in the presence of desiccant at room temperature. The antibodies were obtained from MEDIX Biochemica and Boehringer Mannheim (Indianapolis, Ind.). Other reagents are available from Calbiochem, Sigma and Fluka.

The first and third liquid permeable materials bound together to form the sample treatment pad received conjugate as disclosed in Example 2. The horizontal bar, vertical bar and test complete indicator 58 were applied to the appropriate site with an air brush spotting machine. The horizontal bar 52 was prepared from blue latex. The vertical line 54 was prepared using a rabbit polyclonal antibody to the α fragment of HCG. A sheep anti-Bovine serum albumin solution was applied as a test complete indicator 58 to generate a test complete line and a rabbit IgG solution (4 mg/ml) was used to make an invalid test line.

To assemble the assay, the second liquid permeable material, here a cotton filter, was placed onto the first support tier 40 on the lower casing surface 28. Another multiform end pad (silica gel desiccant, sg-145, 0.057" thickness) was positioned on the second support tier 46. The sample treatment pad 56 was placed on top of the second liquid permeable cotton filter. An 8 μ nitrocellulose membrane was carefully placed on the third support tier such that both ends overlapped with the third liquid permeable material 36 on one end and the absorbant pad 44 on the other. The upper plastic case was snapped into place using a snap and groove lock mechanism positioned at complementary positions along the inner surfaces of the upper and lower casing.

Dimensions of the Exemplary Apparatus associated with the HCG assay:
- Housing Dimensions: 8.5 cm×5.5 cm×0.5 cm
- Sample application well: 0.8 cm (diameter)
- Result window: 1.0 cm×1.0 cm
- Assay complete window: 0.5 cm×0.2 cm
- Second liquid permeable material: 1.6 cm×1.0 cm×0.05 cm
- First liquid permeable material: 1.0 cm×1.0 cm×0.15 cm
- Third liquid permeable material: 1.0 cm×0.3 cm×0.15 cm While particular embodiments of the invention have been described in detail, it will be apparent to those skilled in the art that these embodiments are exemplary rather than limiting, and the true scope of the invention is that defined in the following claims.

What is claimed is:

1. An immunochromatographic assay device for detection of an analyte comprising:

a housing having an opening for introduction of a liquid sample;

first liquid permeable material in said housing under said opening to receive a liquid sample introduced through said opening and defining a sample receiving zone;

second liquid permeable material in said housing under said first liquid permeable material in fluid contact with said first liquid permeable material to receive sample from said first liquid permeable material, said second liquid permeable material being absorbent and defining a sample transport zone;

third liquid permeable material in said housing adjacent said first liquid permeable material and in fluid contact with said second permeable material to receive sample from said second liquid permeable material, said third liquid permeable located on top of said second liquid permeable material;

a barrier comprising a hydrophobic material interposed between said first and third liquid permeable materials to prevent direct transfer of sample from said first liquid permeable material to said third liquid permeable material;

an elongated sheet of wicking material in fluid contact with said third liquid permeable material in fluid contact with said third liquid permeable material to receive sample therefrom, wherein said elongated sheet of wicking material supports an immobilized capture molecule for said analyte; and a detecting reagent located in one of said liquid permeable materials to detect the presence of bound analyte in said elongated sheet of wicking material.

2. The assay device of claim 1, wherein said first and third liquid permeable materials and said hydrophobic material are physically joined together into an integral sheet which is separate from said second liquid permeable material.

3. The assay device of claim 1, wherein said first liquid permeable material is porous thermoplastic polymer.

4. The assay device of claim 3, wherein said third liquid permeable material is porous thermoplastic polymer.

5. The assay device of claim 4, wherein said porous thermoplastic polymer is high density polyethylene.

6. The assay device of claim 4, wherein said first liquid permeable material has a pore size that is smaller than the pore size of said third liquid permeable material.

7. The assay device of claim 1, wherein said first liquid permeable material has a pore size of not greater than about 300 microns and acts to filter said sample.

8. The assay device of claim 1, further comprising an absorbent material in fluid contact with an end of said wicking material which is distal from the end of said wicking material which is in fluid contact with said third liquid permeable material.

9. The assay device of claim 1, wherein said first liquid permeable material has a sufficient pore size to filter said liquid sample or contains a reagent to pretreat said liquid sample.

10. An immunochromatographic assay device for detection of an analyte in a liquid sample comprising a housing, a sample receiving zone in said housing, an elongated sheet of wicking material in fluid communication with said sample receiving zone, wherein said elongated sheet of wicking material supports an immobilized capture molecule for said analyte, and a detecting reagent located in said sample receiving zone to detect the presence of bound analyte in said elongated sheet of wicking material, said sample receiving zone comprising a sample treatment pad having a first liquid permeable material for receiving the liquid sample, a second liquid permeable material in fluid communication with said first liquid permeable material in order to receive sample from said first liquid permeable material, and a third liquid permeable material in fluid communication with said second liquid permeable material and adjacent said first liquid permeable material, wherein a barrier comprising a hydrophobic material is interposed between said first and third liquid permeable materials to prevent direct transfer of sample from said first liquid permeable material to said third liquid permeable material.

11. The assay device of claim 10, wherein said first liquid permeable material has a sufficient pore size to filter said liquid sample or contains a reagent to pretreat said liquid sample.

12. The assay device of claim 9, wherein said liquid sample is pretreated with immobilized antibody in said first liquid permeable material from an animal immunized with a control fluid sample from a human, said control fluid sample comprising a negative control specimen, wherein said control fluid sample does not contain said analyte, said control fluid sample thereby testing negative in an assay performed with said immunochromatographic assay device.

13. The assay device of claim 10, wherein said liquid permeable material is a porous thermoplastic polymer.

14. The assay device of claim 10, wherein said hydrophobic means is polypropylene hot melt adhesive.

15. The assay device of claim 10, wherein said hydrophobic means is a liquid-impermeable thermoplastic polymer.

16. The assay device of claim 10, wherein a further improvement comprises means for preventing flooding in said assay device.

17. The assay device of claim 16, wherein said means for preventing flooding is a divider that controls the flow of liquid from said liquid permeable materials to said wicking material.

18. The assay device of claim 17, wherein said means for preventing flooding flow includes a depression adjacent to said divider to collect liquid pooling in the housing.

19. The assay device of claim 10, wherein said housing additionally comprises at least two support rails extending in the direction of fluid flow for supporting said wicking material, said support rails defining at least one recess between said support rails wherein excess liquid can pool.

20. The assay device of claim 10, wherein said third liquid permeable material has a sufficient pore size to filter said liquid sample or contains a reagent to pretreat said liquid sample.

21. A sample treatment pad for use in an immunochromatographic assay device comprising at least a first liquid permeable material;

a second liquid permeable material in fluid contact with said first liquid permeable material in order to receive sample from said first liquid permeable material, said second liquid permeable material being absorbent and defining a sample transport zone;

a third liquid permeable material adjacent said first liquid permeable material and in fluid contact with said second liquid permeable material in order to receive sample from said second liquid permeable material; and a barrier comprising a hydrophobic material interposed between said first and third liquid permeable materials to prevent direct transfer of sample from said first liquid permeable material to said third liquid permeable material.

22. The sample treatment pad of claim 21, wherein at least one of said liquid permeable materials is a porous thermoplastic polymer.

23. The sample treatment pad of claim 21, wherein said hydrophobic barrier is polypropylene, silicone, or rubber.

24. The sample treatment pad of claim 21, wherein said hydrophobic barrier is high density polyethylene.

25. The sample treatment pad of claim 21, wherein at least one of said liquid permeable materials is a glass fiber pad.

* * * * *

UNITED STATES PATENT AND TRADEMARK OFFICE
CERTIFICATE OF CORRECTION

PATENT NO. : 5,354,692
DATED : October 11, 1994
INVENTOR(S) : Yang, et al

It is certified that error appears in the above-indentified patent and that said Letters Patent is hereby corrected as shown below:

At line 5 of col. 7 please delete " (ICN Biochemicals, Inc., Irvine, Calif.)" and replace with -- (Pall Corporation, Glen Cove, New York) --

Signed and Sealed this

Twenty-fifth Day of April, 1995

Attest:

BRUCE LEHMAN

*Attesting Officer*         *Commissioner of Patents and Trademarks*